United States Patent
Youssefi et al.

(10) Patent No.: US 8,388,610 B2
(45) Date of Patent: Mar. 5, 2013

(54) TREATMENT PATTERN MONITOR

(75) Inventors: Gerhard Youssefi, Landshut (DE); Anton Hilger, Munich (DE)

(73) Assignee: Technolas Perfect Vision GmbH, Munich (DE)

( * ) Notice: Subject to any disclaimer, the term of this patent is extended or adjusted under 35 U.S.C. 154(b) by 0 days.

(21) Appl. No.: 12/962,318

(22) Filed: Dec. 7, 2010

(65) Prior Publication Data
US 2011/0137300 A1 Jun. 9, 2011

Related U.S. Application Data

(63) Continuation of application No. PCT/EP2009/057372, filed on Jun. 15, 2009.

(30) Foreign Application Priority Data

Jun. 16, 2008 (DE) .......................... 10 2008 028 509

(51) Int. Cl.
A61B 18/20 (2006.01)

(52) U.S. Cl. .............................. 606/5; 606/10; 351/200

(58) Field of Classification Search .................... 607/88, 607/89; 606/3–6, 10–12; 128/898; 351/200, 351/205–212
See application file for complete search history.

(56) References Cited

U.S. PATENT DOCUMENTS

| | | | |
|---|---|---|---|
| 5,425,727 A | 6/1995 | Koziol | |
| 5,777,719 A | 7/1998 | Williams | |
| 5,891,132 A | 4/1999 | Hohla | |
| 5,928,221 A | 7/1999 | Sasnett | |
| 5,949,521 A | 9/1999 | Williams | |
| 5,984,916 A | 11/1999 | Lai | |
| 6,033,075 A | 3/2000 | Fujieda | |
| 6,086,204 A | 7/2000 | Magnante | |
| 6,090,100 A | 7/2000 | Hohla | |
| 6,095,651 A | 8/2000 | Williams | |
| 6,132,424 A | 10/2000 | Tang | |
| 6,159,205 A | 12/2000 | Woodward et al. | |
| 6,271,936 B1 | 8/2001 | Yu et al. | |
| 6,325,702 B2 | 12/2001 | Robinson | |
| 6,332,216 B1 | 12/2001 | Manjunath | |
| 6,394,999 B1 | 5/2002 | Williams | |
| 6,413,251 B1 | 7/2002 | Williams | |
| 6,454,761 B1 | 9/2002 | Freedman | |

(Continued)

FOREIGN PATENT DOCUMENTS

DE 19727573 5/1998
DE 20 2005 018911 3/2006

(Continued)

OTHER PUBLICATIONS

PCT International Search Report regarding U.S. Appl. No. 12/962,318; International Application No. PCT/EP2009/057372; International Filing Date: Jun. 15, 2009; Priority Date: Jun. 16, 2008 for Applicant Technolas Perfect Vision GmbH.

(Continued)

Primary Examiner — Ahmed Farah
(74) Attorney, Agent, or Firm — Akin Gump LLP; David R. Clonts

(57) ABSTRACT

The invention relates to an apparatus and a method for determining the applicability of a treatment pattern for manipulation of a cornea of an eye using a laser. The concept of the present invention is based on the determination of an actual volumetric profile based on a set of input data and a theoretical volumetric profile which is created independently based on only the basic optical parameters. On the basis of a comparison of the determined volumetric profiles it is determined whether the actual volumetric profile is within predetermined tolerances.

15 Claims, 1 Drawing Sheet

U.S. PATENT DOCUMENTS

| | | |
|---|---|---|
| 6,500,171 B1 | 12/2002 | Williams |
| 6,508,812 B1 | 1/2003 | Williams |
| 6,511,180 B2 | 1/2003 | Guirao et al. |
| 6,607,521 B2 | 8/2003 | Vinciguerra |
| 6,635,051 B1 | 10/2003 | Hohla |
| 6,715,877 B2 | 4/2004 | Molebny |
| 6,755,819 B1 | 6/2004 | Waelti |
| 6,808,266 B2 | 10/2004 | Youssefi et al. |
| 6,848,790 B1 | 2/2005 | Dick |
| 6,923,802 B2 | 8/2005 | Williams |
| 6,997,555 B2 | 2/2006 | Dick |
| 7,380,942 B2 | 6/2008 | Molebny |
| 2002/0026180 A1 | 2/2002 | Nakamura |
| 2002/0075451 A1 | 6/2002 | Ruiz |
| 2002/0082629 A1 | 6/2002 | Cox |
| 2003/0023233 A1 | 1/2003 | Smith et al. |
| 2003/0048413 A1 | 3/2003 | Ross |
| 2003/0128335 A1 | 7/2003 | Campin |
| 2003/0193647 A1 | 10/2003 | Neal |
| 2004/0002697 A1 | 1/2004 | Youssefi et al. |
| 2004/0021874 A1 | 2/2004 | Shimmick |
| 2005/0159733 A1 | 7/2005 | Dick |
| 2005/0273088 A1 | 12/2005 | Youssefi et al. |
| 2008/0033408 A1 | 2/2008 | Bueler |
| 2008/0058780 A1 | 3/2008 | Vogler |

FOREIGN PATENT DOCUMENTS

| | | |
|---|---|---|
| DE | 10 2005 006897 | 8/2006 |
| EP | 0697611 | 2/1996 |
| EP | 1396244 A2 | 3/2004 |
| EP | 1719483 | 11/2006 |
| JP | 2000300596 | 10/2000 |
| JP | 2002524144 | 8/2002 |
| WO | 9527535 | 10/1995 |
| WO | 9611655 | 4/1996 |
| WO | 9848746 | 11/1998 |
| WO | 2004095187 | 7/2000 |
| WO | 0124688 | 4/2001 |
| WO | 0128410 A | 4/2001 |
| WO | 0128477 A1 | 4/2001 |
| WO | 0234178 | 5/2002 |
| WO | 03068103 | 8/2003 |
| WO | 03075778 | 9/2003 |
| WO | 2004041104 | 5/2004 |
| WO | 2004052253 A1 | 6/2004 |
| WO | 2004053568 | 6/2004 |
| WO | 2005007002 | 1/2005 |
| WO | 2007012924 | 2/2007 |
| WO | 2007143111 | 12/2007 |

OTHER PUBLICATIONS

Damien Gatinel, et al., "Three-dimensional representation and qualitative comparisons of the amount of tissue ablation to treat mixed and compound astigmatism," Journal of Cataract and Refractive Surgery, vol. 28 (No. 11), p. 2026-2034 (Nov. 1, 2002).

US 5,423,802, 06/1995, Marshall (withdrawn)

TREATMENT PATTERN MONITOR

This is a continuation of International Application PCT/EP2009/057372, with an international filing date of Jun. 15, 2009, and which claims the benefit of German Application No. 10 2008 028 509.9, with a foreign filing date of Jun. 16, 2008.

FIELD OF INVENTION

The invention relates to an apparatus and a method for determining the applicability of a treatment pattern for manipulation of a cornea of an eye using a laser. In particular, a treatment to reduce a refractive error of an eye is verified by using independent measures to be within certain tolerances before the actual treatment of the eye.

BACKGROUND OF THE INVENTION

The typical course of the planning phase for a refractive treatment includes, i.a., the upload of input data corresponding to a desired refractive correction, specification of the desired correction, creation of the treatment pattern, and upload of the data onto a therapeutic platform, i.e. a laser treatment system. The desired refractive correction may be based on diagnostic data obtained by at least one of a subjective refractive error and a measured objective refractive error. The measured refractive error may be obtained by at least one of a wavefront sensor, topographical measurement device or a pachymetry measurement device. Low order aberrations may be determined by a subjective refractive error, e.g. considering the verbal feedback of a patient.

The generated corneal shape change profile, e.g. a simulated ablation pattern of an excimer laser or a volumetric femtosecond removal profile, may be disclosed in a graphical user interface GUI or an other implementation. The volumetric profile describes the amount of microns of corneal tissue which is planned to be removed in a certain 3 dimensional location on or in the cornea. Tissue on the cornea, i.e., on the surface of the cornea may be removed, e.g., by an excimer laser and tissue in the cornea, i.e., an intrastromal effect may be caused by a femtosecond laser.

In the determination of a refractive treatment checks may be applied, e.g., whether the corneal thickness after a treatment is still sufficient such that the treatment is applicable. In presently available systems the person controlling a treatment apparatus, usually a physician, finally decides whether a treatment is conducted, i.a., based on a GUI or an other implementation as outlined above.

One of the continuously developing usability and regulatory requirements is to ensure a certain level of usability comfort and applicable safety to the user, i.e., to make refractive treatments safe and more reliable and demonstrate this in an easy but quantitative way to the user. The sole observation of simulated ablation patterns may not be sufficient any more for future applications.

There is a need to provide an independent check that the created ablation pattern is actually related to the desired refractive correction.

Document WO-A-98/40041, from Chiron Technolas GmbH Ophthalmologische Systeme, relates to a simulation of a laser treatment on the eye by pretreating a contact lens. The treated contact lens is placed on the patient's eye and the patient's resulting visual acuity is measured. If within acceptable limits, the treatment is then performed on the patient's eye. Otherwise, the treatment pattern is adjusted.

An aspect of the invention is to provide a method and an apparatus for determining whether the volumetric ablation relating to a certain treatment pattern is within predefined tolerances, i.e., to provide an independent check of the applicability of the created volumetric profile.

SUMMARY

The above objects are achieved by the features of the appended claims. Aspects of the invention are directed to a method and an apparatus for determining the applicability of a treatment pattern for manipulation of the cornea of an eye using a laser, e.g. an excimer laser and/or a femtosecond laser. Further, the invention relates to a treatment pattern calculator and a laser treatment system. The concept of the present invention is based on the determination of an actual volumetric profile and a theoretical volumetric profile, each based on the same data, which correspond to a desired treatment. In particular, the theoretical volumetric profile may be based on one, more or all data from which the actual volumetric profile is determined.

On the basis of a comparison of the actual and the theoretical volumetric profile it is determined whether the actual volumetric profile is within predetermined tolerances, i.e. whether the planned treatment is actually related to the desired refractive correction of an eye. Only when this check is satisfactory the treatment pattern is used for performing a treatment of the eye. The method may be implemented into a refractive device, e.g. a treatment system and/or a treatment pattern calculator, to provide an independent check of the created volumetric profile.

According to one aspect, a treatment pattern is developed based on a set of input data corresponding to a desired refractive correction. An actual volumetric profile is determined based on said treatment pattern. Further, a theoretical volumetric profile is determined based on at least one of said set of input data by using a basic theoretical model. In other words, the theoretical volumetric profile is based on at least a part of the same data as the actual volumetric profile, preferably based on only the basic optical parameters. However, the theoretical volumetric profile is developed independently from the latter. For example, the theoretical volumetric profile may be based on the sphere, the cylinder and/or the optical zone as one of said input data. The actual volumetric profile is compared with the theoretical volumetric profile and it is determined whether the actual volumetric profile is within specified tolerances on the basis of the theoretical volumetric profile.

According to the invention a basic theoretical model is generated, e.g. depending on the origin of the volumetric profile, which approximates the shape of an actually created volumetric profile. The shape can be described by different parameters such as the maximum ablation depth and/or the central ablation depth and/or the treatment area and/or the ablation volume and/or the amount of correction in diopters of the volumetric pattern and/or the difference and/or ratio of a central ablation depth and an ablation depth in a defined area and/or the difference and/or ratio of minimum or maximum ablation depth in defined areas.

A slight modification of at least one of these parameters of the theoretical model creates in minimum two theoretical volumetric profiles, which may serve as minimum and maximum tolerance limits, so-called estimators, for the actually generated volumetric profile.

Dependent on the spacing, i.e. the difference of the modified parameters, more or less detailed statements can be created which indicate the over or under correction potential of the actually generated volumetric profile. The narrower the spacing of the modified parameters, i.e., the smaller the tolerance range, the better the actual effect of the treatment pattern can be determined. The better the actual effect of the treatment pattern can be determined, the better a potential treatment error can be identified.

The final outcome of the method/apparatus according to the invention may be the statement that the generated volumetric profile is applicable/not applicable and/or is within predefined limits ±X % or ±X Diopters of the desired treatment or exceeds the predefined limits ±X % or ±X Diopters.

This method can be applied to standard non personalized treatments as well as to personalized treatments in which certain diagnostic maps such as wavefront, topography, pachymetry (usefull for femtosecond laser applications) or combinations of them are used.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1:
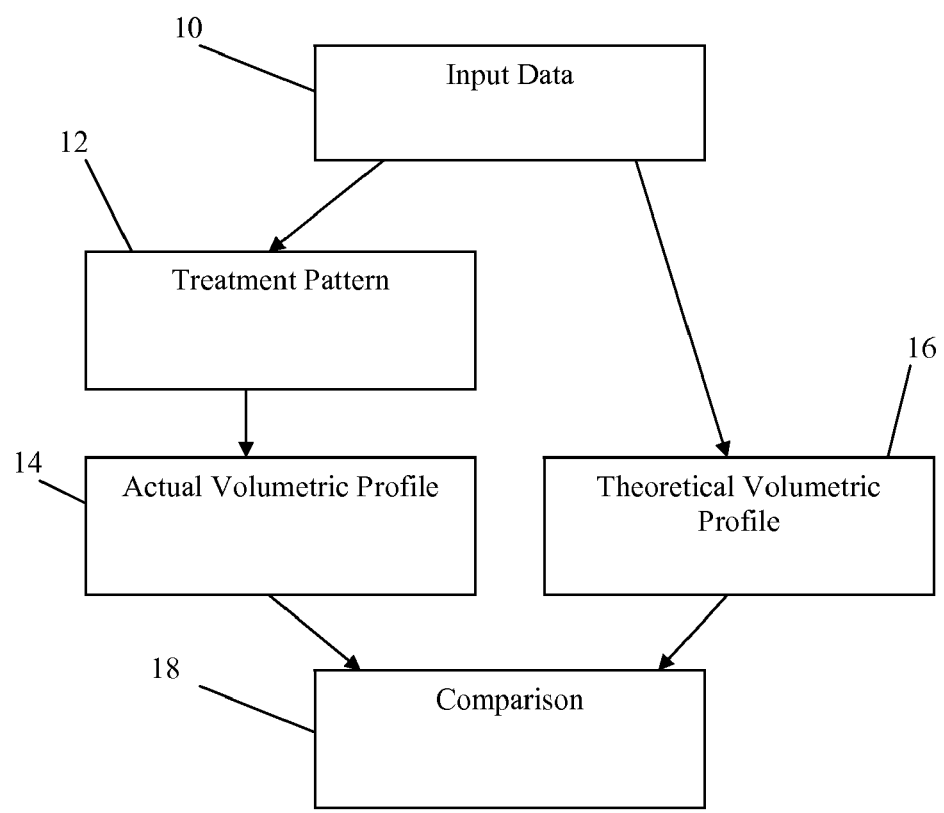
FIG. 1 is a block diagram of the method for determining the applicability of a treatment pattern according to the invention.

FIG. 1 shows a block diagram of the method according to the invention. Input data 10 relate to a desired refractive correction. It is noted that the present invention is not limited to one or more methods for determining a desired refractive correction. In fact, the type of determination does not affect the applicability of the present invention.

Based on the input data 10, a treatment pattern 12 is developed. An exemplary simple case is represented in a standard non aspheric excimer laser treatment pattern such as Bausch & Lomb's PlanoScan or TissueSaving. A typical treatment pattern for these two classes of ablation algorithms may be based on the subjective refraction expressed in subjective sphere $S_{subj}$, subjective cylinder $C_{subj}$, subjective axis of the cylinder $A_{subj}$ and the desired optical zone OZ of the treatment. In the case of the TissueSaving algorithm additional parameters such as the central preoperative topographical K-Reading $K_{pre}$ can be added.

Based on the treatment pattern 12 an actual volumetric profile 14 is determined. The actual volumetric profile 14 may represent the amount of ablated corneal tissue to apply a desired refractive correction to a cornea of an eye. It is noted that in the context of the present invention any refractive manipulation of the eye may be considered for determining the applicability of a treatment. Known manipulations are, e.g., ablation by an excimer laser or intrastromal manipulation by a femtosecond laser.

To provide an independent check of the delivered refractive correction in the case of an application of the treatment pattern 12 to a corneal surface, an independent estimator is needed. The estimator is determined independently of the treatment pattern calculation to evaluate the contained refractive power, i.e. the amount of correction in diopters D, in the actual volumetric profile 14.

A theoretical volumetric profile 16 is determined based on one, more or all of said input data using a basic theoretical model. For the cases mentioned above (PlanoScan and TissueSaving) a toric or non-toric thin lens formula as basic theoretical model may be an appropriate estimator. With this estimator the above mentioned parameters which describe the shape of the treatment pattern, such as maximum and central ablation depth, can be derived independently from the actual used PlanoScan or TissueSaving algorithm.

The power, i.e. the amount of correction in diopters D, and the optical zone of the thin lens formula may be modified successively to provide a best match up to a certain tolerated deviation expressed in dioptres of spherical equivalent. This may be ±1.0 D, ±0.5 D, ±0.33 D or even ±0.25 D.

In the case of the spherical equivalent this range is directly dependent on the amount of desired astigmatic correction, as a rotationally symmetric profile is used to approximate a toric profile. The optical zone may be approximated in 1.00mm steps or even smaller steps such as 0.75 mm, 0.50 mm or 0.25 mm.

A more detailed implementation may use toric estimators to create a set of parameters to describe the shape of upper and lower limits. The actual volumetric profile 14 must be within the two created lower and higher estimators. Having this condition creates a simple decision process, based on a comparison 18 of the actual volumetric profile 14 with the theoretical volumetric profile 16, whether the created ablation profile is within the pre specified tolerances of the desired correction or not, i.e., whether the determined treatment pattern 12 relating to the actual volumetric profile 14 is applicable or not.

In general, two different strategies may be considered to create a statement about the contained power, i.e. the amount of correction in diopters D, in an actual volumetric profile 14.

First Strategy (Fixed Tolerance)

Figure 2:
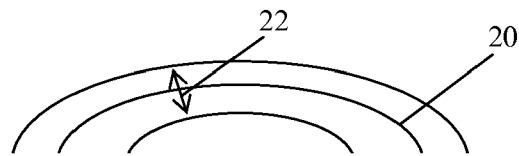
FIG. 2 is a schematic sectional view of a simulated postoperative cornea with a tolerance range according to the invention.

FIG. 2 shows a predefined tolerance range 22, which may be used to evaluate whether the created actual volumetric profile 14, leading to a post-operative corneal surface 20, is consistently within this tolerance range. In the first strategy fixed threshold values may be used for at least one of the tolerated deviation in sphere $\Delta S_{subj}$, cylinder $\Delta C_{subj}$, axis of the cylinder $\Delta A_{subj}$ and the desired optical zone $\Delta OZ$.

A lower Estimator can be given by the following parameters:

$$S_{subj,\,low} = S_{subj} - \Delta S_{subj}$$

$$C_{subj,\,low} = C_{subj} - \Delta C_{subj}$$

$$A_{subj,\,low} = A_{subj}$$

$$OZ_{low} = OZ - \Delta OZ$$

The higher Estimator can be given by the following parameters:

$$S_{subj,\,high} = S_{subj} + \Delta S_{subj}$$

$$C_{subj,\,high} = C_{subj} + \Delta C_{subj}$$

$$A_{subj,\,high} = A_{subj}$$

$$OZ_{high} = OZ + \Delta OZ$$

According to this example the values for sphere, cylinder and optical zone may be changed at the same time to get the lower and higher estimator. Overall different combinations of values might be changed to create the estimators. Only sphere might be changed and cylinder and optical zone might be unchanged, only optical zone might be changed and the refraction unchanged, axis of cylinder might be changed and all other values unchanged. Thus, at least one of the before mentioned variables may be changed.

According to an aspect of the invention it is determined whether the actual volumetric profile 14 is within the two created lower and higher estimators defining the predefined tolerance range 22. Based on the comparison 18 a statement is created that the actual volumetric profile 14, leading to the post-operative corneal surface 20, does/does not deliver a refractive correction which is within the accepted tolerances. Also more than one lower and one higher tolerance level can be determined to provide a more detailed information about the effect of the actual volumetric profile 14.

Second Strategy (Minimal Tolerance)

According to the second strategy, at least one of the threshold values for the tolerated deviation in sphere $\Delta S_{subj}$, cylinder $\Delta C_{subj}$, axis of the cylinder $\Delta A_{subj}$ and the desired optical zone $\Delta OZ$ can be optimised to provide the minimal deviation from the actual ablation profile, which may be accomplished iteratively (not shown in FIG. 1).

The result from this strategy are minimal detected deviations in sphere, cylinder, axis and optical zone which may still allow an upper and lower estimation of the refractive power of the actual volumetric profile 14. In particular, in case the comparison 18 provides a difference between the actual volumetric profile 14 and the theoretical volumetric profile 16 which is greater than an approximation step of the theoretical volumetric profile 16, the latter profile is amended to reduce the tolerance range and compared again with the actual volumetric profile 14. In other words, one or more parameters of the theoretical volumetric profile 14 are successively modified to approximate the theoretical volumetric profile (16) to the actual volumetric profile (14).

Both described strategies can be used in more complex ablation procedures. So in the case of aspheric ablation profiles in which a certain offset on spherical aberration is added to the basic sphero cylindrical profile, this component will be added to the theoretical estimator formula.

In other words the estimator in these cases may be the appropriate thin lens formula plus the pre defined spherical aberration. In even more complex ablation strategies such as wavefront driven ablations, a mean sphero cylindrical profile using a thin lens formula or in a further implementation an aspheric thin lens formula may be used. In the case of specific questions even individual high order components may be used to evaluate for example the total amount of coma or higher order aberration information such like HORMS or 3rd order RMS or 4th order RMS or 5th order RMS contained in a specific ablation profile.

Both mentioned strategies can also be used to create specific statements on a sub group of parameters down to only one specific parameter. One exemplary possibility can be to only check the applicability of a treatment pattern with reference to the delivered optical zone.

It needs to be reiterated, that the invention is not limited to an excimer laser treatment pattern. As soon as the actual volumetric profile 14 is given, the estimator can be determined. In a more general interpretation of this concept, the estimator may be applied to a simulated post-operative corneal profile, which is given based on the pre-operative diagnostic data (for example from the Next Generation Diagnostic Instrument NGDI, Bausch & Lomb) and a volumetric ablation profile given by an excimer laser or a femtosecond laser.

The above described method may be implemented in a treatment calculator or a laser software where a treatment file is uploaded to provide an independent check of the outcome of the treatment calculator. Such a treatment calculator or an apparatus for conducting the above method may be implemented in a laser treatment system, e.g., with an excimer laser and/or a femtosecond laser.

While certain embodiments have been chosen to illustrate the invention it will be understood by those skilled in the art that changes and modifications can be made therein without departing from the scope of the invention as defined in the appended claims. In particular it is noted that even though exemplary reference was made to an myopic vision error also other vision errors will benefit from the present invention.

What is claimed is:

1. A computer system for determining the applicability of a treatment pattern for manipulation of a cornea of an eye using a laser, the computer system capable of:
   (a) receiving input data corresponding to a desired refractive correction and developing a treatment pattern from the input data;
   (b) developing an actual volumetric profile from the treatment pattern;
   (c) receiving a theoretical volumetric profile wherein the theoretical volumetric profile is based on the input data and developed from a basic theoretical model; and
   (d) comparing the actual volumetric profile with the theoretical volumetric profile to determine whether the actual volumetric profile is within specified tolerances on the basis of the theoretical volumetric profile.

2. The system of claim 1, wherein the theoretical model uses a number of basic parameters, and wherein the computer system is further capable of determining a first theoretical volumetric profile when using the basic parameters of the theoretical model and determining a second theoretical volumetric profile using said theoretical model wherein at least one of the number of basic parameters is modified.

3. The system of claim 2, wherein the computer system is further capable of comparing the actual volumetric profile with the first theoretical volumetric profile which serves as a minimum estimator and comparing the actual volumetric profile with the second theoretical volumetric profile which serves as a maximum estimator.

4. The system of claim 3, wherein the computer system is further capable of modifying at least one of the basic parameters to determine a limit of a potential over or under correction of the actual volumetric profile.

5. The system of claim 2, wherein the basic parameters are at least one of a maximum ablation depth, a central ablation depth, a treatment area, an ablation volume, an amount of correction in diopters of the volumetric pattern, a difference and/or ratio of a central ablation depth and an ablation depth in a defined area, or a difference and/or ratio of minimum or maximum ablation depth in defined areas.

6. The system of claim 1, wherein the computer system is further capable of determining whether the actual volumetric profile corresponds to the desired refractive correction.

7. The system of claim 1, wherein the basic theoretical model is a toric or nontoric thin lens formula.

8. The system of claim 7, wherein the computer system is further capable of modifying an amount of correction in diopters and/or an optical zone of the thin lens formula to approximate the theoretical volumetric profile to the actual volumetric profile.

9. The system of claim 8, wherein the amount of correction in diopters is one of ±1.0 D, ±0.5 D, ±0.33 D or ±0.25 D.

10. The system of claim 8, wherein the modification of the optical zone is one of 1.00 mm, 0.75 mm, 0.50 mm or 0.25 mm.

11. The system of claim 1, wherein the specified tolerance is a fixed tolerance, preferably at least one of a tolerated deviation in sphere, cylinder, axis, and optical zone.

12. The system of claim 1, wherein the specified tolerance is a minimal tolerance, preferably by optimizing the tolerated deviation in sphere, cylinder, axis and optical zone to provide the minimal deviation from the actual volumetric profile.

13. The system of claim 1, wherein said computer system is a laser treatment system.

14. The system of claim 1, wherein said computer system includes a treatment calculator.

15. The system of claim 14, wherein the treatment calculator determines a treatment pattern from diagnostic data.

\* \* \* \* \*